United States Patent [19]

Vohra et al.

[11] Patent Number: 5,178,793

[45] Date of Patent: Jan. 12, 1993

[54] FERROELECTRIC LIQUID CRYSTAL COMPOUNDS AND COMPOSITIONS

[75] Inventors: Rohini T. Vohra; David M. Walba; Michael D. Wand, all of Boulder, Colo.

[73] Assignee: University Research Corporation, Boulder, Colo.

[21] Appl. No.: 360,397

[22] Filed: Jun. 1, 1989

[51] Int. Cl.$^5$ .................. C09K 19/34; C07D 239/02; C07D 213/00; C07D 211/72

[52] U.S. Cl. .................. 252/299.61; 252/299.66; 252/299.67; 544/318; 544/335; 546/1; 546/290; 546/301

[58] Field of Search .................. 252/299.01, 299.61, 252/299.66, 299.67; 549/556, 557, 559; 544/335, 318; 546/290, 1, 301

[56] References Cited

U.S. PATENT DOCUMENTS

| | | | |
|---|---|---|---|
| 4,638,073 | 1/1987 | Walba et al. | 252/299.61 |
| 4,789,751 | 12/1988 | Walba et al. | 252/299.01 |
| 4,835,295 | 5/1989 | Walba et al. | 549/557 |
| 4,876,026 | 10/1989 | Saito et al. | 252/299.61 |
| 4,876,028 | 10/1989 | Hemmerling et al. | 252/299.61 |
| 4,909,957 | 3/1990 | Sakaguchi et al. | 252/299.61 |
| 4,973,425 | 11/1990 | Kazuhiko et al. | 252/299.61 |

OTHER PUBLICATIONS

Walba et al., (1986) J. Amer. Chem. Soc. 108:7424–7425.

Hemmerling et al., (1988) European Patent Application, Publication No. 263437.
Pp. 149–151 from Banks, James E., "*Naming Organic Compounds*" 2nd Edition, entitled Kinds of Systematic Nomenclature and Construction of Names.
Chemical Abstract 109:119866w.
Chemical Abstract 111:87594d.

*Primary Examiner*—Robert L. Stoll
*Assistant Examiner*—Philip Tucker
*Attorney, Agent, or Firm*—Greenlee & Winner

[57] ABSTRACT

Chiral, nonracemic compounds of the general formula:

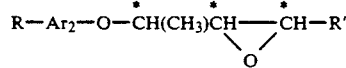

in which the chiral tail group containing three asymmetric carbons (as indicated by *) is incorporated into a suitable FLC core moiety R—Ar$_2$ are provided. The Ar$_2$ core can include phenylbenzoate, biphenyl, phenylpyridine or phenylpyrimidine. R is an alkyl or alkoxy group having three to fifteen carbon atoms and R' is an alkyl group having from three to twelve carbon atoms. The compounds are useful as ferroelectric liquid crystal components having high polarization density. Compounds in which the chiral epoxide tail is the 1R-methyl-2S,3S-epoxy or 1S-methyl-2R,3R-epoxy enantiomer having higher polarization density.

26 Claims, No Drawings

FERROELECTRIC LIQUID CRYSTAL COMPOUNDS AND COMPOSITIONS

This invention was made with partial support of the United States Government which has certain rights in this invention.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. Since the coupling to an applied electric field by this mechanism is rather weak, the resultant electro-optical response time may be too slow for many potential applications.

Liquid crystal displays have a number of unique characteristics, including low voltage and low power of operation, which makes them perhaps the most promising of the non-emissive electro-optical display candidates available with today's technology. However, slow response and insufficient nonlinearity can impose limitations for many potential applications. The requirement for speed may become especially important in proportion to the number of elements which have to be addressed in a device. This may result in increasingly impractical production costs for the potential use of such devices in flat-panel displays for use in video terminals, oscilloscopes, radar and television screens.

It has been shown by N. A. Clark and S. T. Lagerwal in Appl. Phys. Lett. 36:899 (1980) and in U.S. Pat. No. 4,367,924 that electro-optic effects with sub-microsecond switching speeds are achievable using the technology of ferroelectric liquid crystals (FLCs). Some display structures prepared using FLC materials, in addition to the high speed (about 1,000 times faster than currently used twisted nematic devices) reported by these investigators, also exhibit bistable, threshold sensitive switching, making them potential candidates for light modulation devices including matrix addressed light valves containing a large number of elements for passive displays of graphic and pictorial information, as well as for optical processing applications.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwal, appropriate application of an external electric field results in alignment of the molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains a 2-methylbutyl chiral tail. Pure DOBAMBC exhibits a smectic C* phase with a ferroelectric polarization of $-3$ nC/cm$^2$.

There are several reports of compounds containing phenylbenzoate and related cores coupled to chiral tail units which possess monotropic smectic C* phases displaying fast switching speeds at room temperature, or which can be employed as FLC dopants to induce high polarization and fast switching speeds when combined in mixtures with FLC host materials. Walba et al., U.S. Pat. No. 4,556,727 reports phenylbenzoates having non-racemic 2-alkoxy-1-propoxy tails. Eidman and Walba, U.S. Pat. No. 4,777,280 report chiral 1-cyanoalkoxy phenylbenzoates. Walba and Razavi, U.S. Pat. No. 4,695,650 report chirally asymmetric reverse ester phenylbenzoates having chiral 1-haloalkyl tail units.

In related work, Walba et al. (1986) J. Amer. Chem. Soc. 108:7424–7425 and Walba and Vohra, U.S. Pat. No. 4,648,073 and U.S. Pat. No. 4,705,874 disclose ferroelectric (chiral) smectic liquid crystal compounds having an achiral core and chiral tail units derived from (2,3)-alkyloxiranemethanols which possess a high ferroelectric polarization density. The ferroelectric liquid crystal materials reported have the following general formulas:

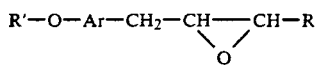

where R is an alkyl of one to seven carbon atoms and R' is an alkyl of five to twelve carbon atoms and Ar is phenylbenzoate or biphenyl.

Hemmerling et al. (1988) European Patent Application, Pub. No. 263437 refers to chiral aryl-2,3-epoxyalkylethers FLC compounds having phenylpyrimidine or phenylpyridazine cores of the formula:

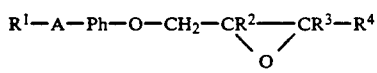

where A is a diazine-2,5,-diyl or diazine-3,6-diyl, $R^1$ is a straight chain or branched alkyl group having 1-12 carbon atoms wherein one or two non-neighboring $CH_2$ groups is replaced with an O or S atom, $R^{2-4}$ are, independent of one another, H, a straight chain alkyl group having 1-12 carbon atoms or a branched alkyl group having 3-10 carbon atoms wherein $R^1$, $R^2$ and $R^3$ are not all H. Compounds in which $R^2$ and $R^3$ are both H having extrapolated polarization densities ($P_{ext}$) in the range from 30-70 nC/cm2 are reported.

Walba and Razavi, U.S. Pat. No. 4,835,295, discloses chirally asymmetric phenyl and biphenylbenzoates having chiral 2,3-epoxy alkyl or 1-halo-2,3-epoxy alkyl tails which are useful as components of FLC materials. The compounds disclosed have the formula:

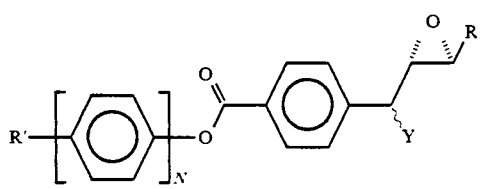

where R' is an alkyl or alkoxyl group having three to fifteen carbon atoms, R is an alkyl group having three to fifteen carbon atoms, n=1 or 2, and Y is a halogen or hydrogen. It is also disclosed, therein, that 1-haloepoxides of formula A can impart higher polarization densities and higher switching speeds in FLC mixtures than their diastereomers of formula B. It is suggested that the difference in properties of A and B is due to the relative alignment of the epoxide and halogen bond dipoles in the isomer.

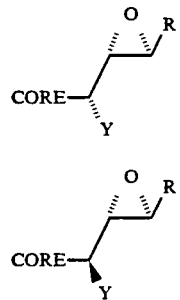

Wand and Walba U.S. Pat. No. 5,051,506, 1988 report chirally asymmetric FLC materials having 2-haloalkoxy, 2,3-dihaloalkoxy or 2,3,4-trihaloalkoxy tails incorporated into a suitable core such as those based on biphenyl, phenylbenzoate, biphenyl benzoate or phenyl pyrimidine moieties. In the case of compounds with chiral dihalide and trihalide tails, it was found that the magnitude of $P_{ext}$ was different for different diasteriomers. Dihalides having the (2R, 3R) or (2S, 3S) configuration had significantly higher $P_{ext}$ than the analogous (2R, 3S) or (2S, 3R) diasteriomers. This effect is attributed to the alignment of the halogen dipoles in the different diasteriomers.

Ohno et al. (1989) U.S. Pat. No. 4,795,587 refers to liquid crystal compounds exhibiting smectic C phases which contain a phenylpyridine core having the formula:

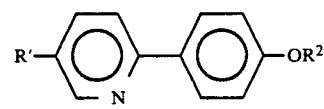

where $R^1$ is an alkyl group having seven to twelve carbon atoms and $R^2$ is an alkyl group having five to twelve carbon atoms.

While a number of useful ferroelectric liquid crystal materials (both pure compounds and mixtures) have been reported, there is a growing need for FLC materials with varying properties of temperature range, tilt angle and switching speed for use in varied applications. Further, there is a need for FLC dopants with varying mixing properties for use in the preparation of FLC mixtures. FLC dopants which impart high polarization density to, and retain low viscosity in, such mixtures are of particular interest.

SUMMARY OF THE INVENTION

The present invention provides a class of chirally asymmetric molecules which are useful as components of ferroelectric liquid crystal materials. These compounds can impart the properties of high ferroelectric polarization density and fast electro-optical switching speeds to low polarization materials when mixed with such materials to form ferroelectric liquid crystal compositions. Alternatively, certain of the compounds of the present invention in pure form may also possess stable smectic C* phases having high polarization density.

The compounds of the present invention are prepared by the incorporation of enantiomerically enriched tail units derived from trans-1-methyl-(2,3-epoxy)-alcohols into a suitable liquid crystal core, such as those cores based on a biphenyl, phenylbenzoate, phenylpyrimidine, phenylpyridine or related structure. More specifically, attachment of enantiomerically enriched trans-1-methyl-(2,3-epoxy)alkoxy tails to the para position of such liquid crystal core units results in compounds which are useful in the preparation of ferroelectric liquid crystal materials, either in pure form or as a component in an FLC mixture.

Specifically, the present invention provides chiral nonracemic trans-1-methyl(2,3-epoxy)alkoxy compounds of the formula:

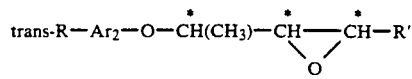

having three asymmetric carbons indicated by * wherein Ar$_2$ is a phenylbenzoate, biphenyl, phenylpyrimidine or phenylpyridine, R is an alkyl or alkoxy group containing three to fifteen carbon atoms and R' is an alkyl group containing three to twelve carbon atoms. The alkyl and alkoxy groups may be straight chain or branched. When Ar$_2$ is phenylbenzoate or biphenyl, it is preferred that R is an alkoxy group. When Ar$_2$ is phenylpyrimidine or phenylpyridine, preferred alkyl and alkoxy groups for R are those containing eight to twelve carbon atoms. It is preferred that R' is an alkyl group containing three to seven carbon atoms.

In one embodiment, the present invention provides chiral nonracemic trans-1-methyl(2,3-epoxy)alkoxy compounds of the formula:

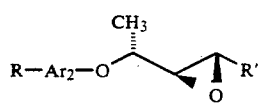

wherein Ar$_2$ is a phenylbenzoate, biphenyl, phenylpyrimidine or phenylpyridine, R is an alkyl or alkoxy group containing three to fifteen carbon atoms and R' is an alkyl group containing three to twelve carbon atoms. The alkyl and alkoxy groups may be straight chain or branched. When Ar$_2$ is phenylbenzoate or biphenyl, it is preferred that R is an alkyoxy group. When Ar$_2$ is phenylpyrimidine or phenylpyridine, preferred alkyl and alkoxy groups for R are those containing eight to twelve carbon atoms. It is preferred that R' is an alkyl group containing three to seven carbon atoms.

An important feature of the present invention is the finding that the 1-methyl compounds of formula II, the "anti" configuration, have much higher extrapolated polarization densities than those of the analogous "syn" diastereomers of formula III. This effect is believed to result from the relative alignment of the ether and epoxy oxygen atoms of the chiral tail in the sterically preferred configuration of the different diastereomers.

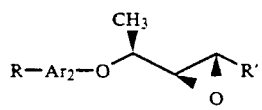

In specific embodiments the present invention provides chiral nonracemic compounds in which 4'-([1R,4-dimethyl-(2S,3S-epoxy)]pentyloxy)phenyl-4-(n-decyloxy)benzoate, designated MDW 155; 4'-([1S,4-dimethyl-(2S,3S-epoxy)]pentyloxy)phenyl-4-(n-decyloxy)benzoate, designated MDW 156; 4'-n-octyloxy-4-[1R,4-dimethyl-(2S,3S-epoxy)]pentyloxybiphenyl, designated MDW 163; 5-n-nonyl-2(4-]1R,4-dimethyl-2S,3S-epoxypentyloxy]phenyl)pyrimidine, designated MDW 165; and 5-n-nonyl-2(4-[1R,4-dimethyl-2S,3S-epoxypentyloxy]phenyl)pyridine, designated MDW 164, are the predominant enantiomers.

In a second aspect, the present invention provides chirally asymmetric nonracemic trans-1-methyl-(2,3-epoxy)alcohols:

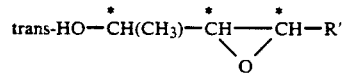

which are useful in the synthesis of ferroelectric liquid crystal compounds or components. These compounds are important in the synthesis of chiral FLC trans-1-methyl-2,3-epoxides of formula I and II. For synthesis of the FLC materials of the present invention trans-1-methyl-2,3-epoxy alcohols in which R' is an alkyl group having from three to twelve carbon atoms are preferred, with those having three to seven carbons being more preferred. For synthesis of the higher polarization density diastereomer of formula II, the 1R-methyl-2S,3S-epoxy and 1S-methyl-2R,3R-epoxy alcohol enantiomers are preferred.

In a specific embodiment the present invention provides chiral nonracemic 1R,4-dimethyl-2S,3S-epoxypentanol or 1S,4-dimethyl-2S,3S-epoxypentanol.

DETAILED DESCRIPTION OF THE INVENTION

The ferroelectric liquid crystal compounds of the present invention are prepared according to the following general reaction scheme:

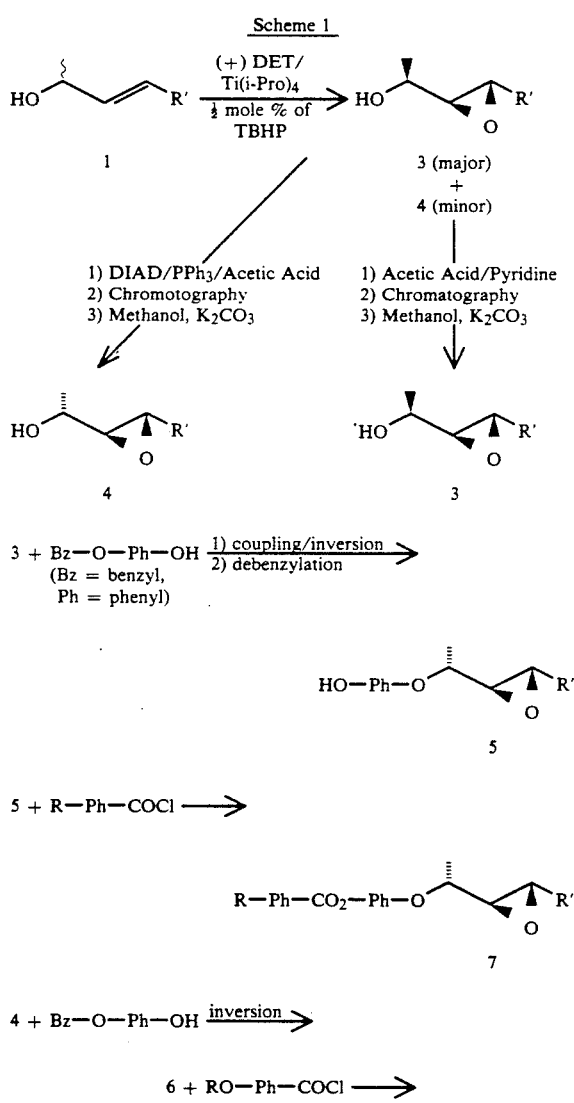

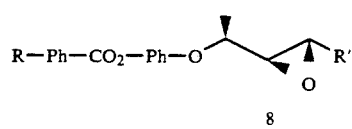

-continued
Scheme 1

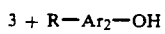
3 + R—Ar₂—OH  →(inversion)
9 (Ar₂ = biphenyl, phenylpyrimidine phenylpyridine)

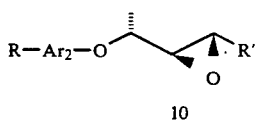
10

4 + R—Ar₂—OH  →(inversion)→ R—Ar₂—O... R'
9
11

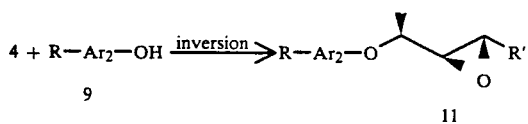

In general terms the chiral nonracemic methylepoxy alcohols of formulas 3 and 4 are prepared by initial enantioselective epoxidation of the racemic methyl allylic alcohol (1) employing procedures described by Katsuki and Sharpless (1980) J. Amer. Chem. Soc. 102:5976; Martin et al. (1981) 103:6237–6240 and U.S. Pat. No. 4,471,130 to give the chiral nonracemic alcohol 3 as the major product. This step also produces small amounts of the diastereomeric alcohol 4 and can produce small amounts of the enantiomer of 3. The diastereomeric alcohols 3 and 4 are difficult to separate. Diastereomerically pure 3 is obtained by conversion of the impure alcohol to the diastereomeric acetates, followed by chromatographic separation of the diastereomeric acetates and removal of the acetate group. Diastereomerically pure 4 is obtained by conversion of the impure alcohol (3) to the acetate of 4 (major product) by inversion at C-1, followed by chromatographic separation of the diastereomeric acetates and removal of the acetate group.

The phenylbenzoate methyl epoxyalkoxides and the biphenyl methyl epoxyalkoxides were prepared by procedures analogous to those described by Walba and Vohra, U.S. Pat. No. 4,638,073 and U.S. Pat. No. 4,705,874. Coupling of p-benzyloxyphenol with the diasteromerically pure methylepoxy alcohols, 3 and 4, using DIAD (or analogous reagents) and PPh₃ proceeds with inversion at C-1 of the tail and subsequent debenzylation gives the methyl epoxyalkoxy phenols, 5 and 6, respectively. The phenylbenzoate methyl epoxyalkoxides (7 and 8) are then prepared by reaction of the phenols with substituted benzoylchloride. The biphenyl methyl epoxyalkoxides (10 and 11 were Ar₂ is biphenyl) are prepared by coupling (with inversion at C-1 of the tail) of the diasteromerically pure methyl epoxyalcohols (3 or 4) to an appropriately substituted biphenol (9), where Ar₂ is biphenyl, employing DIAD and PPh₃. Analogous coupling reactions (with inversion) using DIAD and PPh₃ are employed to prepare the phenylpyrimidines (10 and 11, where Ar₂ is phenylpyrimidine) and phenylpyridines (10 and 11, where Ar₂ is phenylpyridine) methyl epoxyalkoxides from the substituted phenols 9, where Ar₂=phenylpyrimidine and phenylpyridine, respectively. R substituted pyridine phenols are prepared by known procedures such as those described in Ohno et U.S. Pat. No. 4,795,587. R substituted pyrimidine phenols are prepared by known procedures such as those reported in Boller et al. (1978) Z. Naturforsch. 33b:433–438. R substituted phenols are either available from commercial sources or are readily prepared by methods known to the art. For example, the preparation of a number of 4-alkoxyphenols is described in Neubert et al. (1978) Mol. Crys. Liq. Cryst. 44:197–210. Substituted alkoxy biphenols can be prepared by analogous methods. Alkyl phenols and alkyl biphenols of formula 9 can also be prepared by methods known to the art.

Scheme 1 shows the synthesis of 1S-methyl-2S,3S-epoxy and 1R-methyl-2S,3S-epoxy alcohol diastereomers. The enantiomeric 1R-methyl-2R,3R-epoxy and 1S-methyl-2R,3R-epoxy alcohols are prepared by analogous methods substituting diethyl-D-tartrate in the enantioselective epoxidation. Compounds of formulas 3, 8, 10 and 11 represent one of a pair of enantiomers. For illustration, the structure of the enantiomers of the methyl epoxyalkoxide 10 are given:

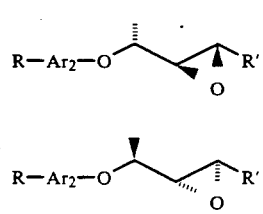

A

B

Enantiomers A and B will function in FLC materials in an equivalent manner, except that the sign of P will be reversed. The compounds of the present invention are diastereomerically pure. The enantiomeric purity of the compounds of the present invention is believed to be high; however, small amounts of enantiomeric products can be produced during synthesis. High enantiomeric purity is preferred to achieve maximum polarization densities, however, the compounds of the present invention need not be enantiomerically pure to be useful in FLC materials. The compounds of the present invention need only be chiral and nonracemic.

Table 1 summarizes phase diagrams, polarization densities and tilt angles of some exemplary FLC mixtures in W82. In Table 1, the phases are noted as X=crystal, I=isotropic liquid, A=smectic A, C*=chiral smectic C, N*=chiral nematic and phase transition temperatures are given in °C. Polarization densities (P) are given in $nC/cm^2$ and the magnitude of P was measured by integration of the dynamic current response to a surface stabilized ferroelectric liquid crystal cell on reversing the applied electric field using a slight modification of the standard methods of Martinot-Lagarde (1976) supra and Martinot-Lagarde (1977) supra. The polarization reversal current was measured after applying a triangular wave form (±15 volts) across a 2.5 μm (using Polyimide spacers) polymer aligned (DuPont Elvamide 8061) SSFLC cell (Patel, J. S. et al. (1986) J. Appl. Phys. 59:2355; Flatischler, K. et al., (1985) Mol. Cryst. Liq. Cryst. 131:21; Patel, J. S. et al. (1984) Ferroelectrics 57:137) with indium-tin oxide (ITO) conducting glass electrodes. The signal (current v. time) was digitized using a Sony/Tektronix 390AD programmable digitizer. The current waveform showed a peak characteristic of the polarization reversal; this current peak was integrated. Division of the value of this integration (charge) by the active are of the cell afforded the magnitude of ferroelectric polarization. For all measurements, the diameter of the ITO coated area of the cell was 0.50 inch. The sign of the polarization was determined directly from observation of molecular orientation in SSFLC cells upon application of electric fields. The optical tilt angle was determined by rotating the shear or polymer aligned cell until extinction was obtained. The polarity of the cell was reversed and the cell was rotated by a measured angle to obtain extinction again. The angle by which the cell was rotated is equal to $2\theta$. The tilt angle was obtained by dividing this angle by two. Tilt angles were measured at $T_c-T_x$, where $T_c$ and $T_x$ are the upper and lower transition temperatures for the C phase, respectively.

the relative alignment of the epoxy and ether oxygens in the tail in the preferred configuration of the diastereomers with the FLC phase. In the diastereomers of formula II, the oxygen dipoles are alligned in the same direction with respect to the smectic tilt plane, resulting in the observed higher polarization density of these diastereomers. It is believed that oxygen dipole alignment in the diastereomers of formula II is influenced by the steric effect of the C-1 methyl group. The difference in polarization between isomers of formula II and III is

TABLE 1

| \multicolumn{6}{c}{FLC Properties of Mixtures of Methyl Epoxides in W82} |
| Dopant | Weight % | P | P(ext) | Tilt angle[1] | Phase Diagram[2] |
|---|---|---|---|---|---|
| MDW 155 | 10% | +10.7 | +107 | 28 | $X \xleftarrow{\leq 36} C^* \xleftarrow{69} A \xleftarrow{72} I$ |
|  | 20% | +25.1 |  | 33 | $X \xleftarrow{27} C^* \xleftarrow{61} A \xleftarrow{63} N \xleftarrow{65} I$ |
|  | 50% | +59.6 |  | 30.5 |  |
| MDW 156 | 10% | −0.53 | −5.3 | 30.5 |  |
|  | 20% | −1.27 |  | 23.5[3] | $X \xleftarrow{22} C^* \xleftarrow{49} A \xleftarrow{61} I$ |
|  | 50%[4] |  |  |  |  |
| MDW 165 | 10% | +13.5 | +135 | 28 | $X \xleftarrow{18} C^* \xleftarrow{55} A \xleftarrow{62.5} I$ |
| MDW 163 | 10% | +13.9 | +139 | 30 | $X \xleftarrow{23} C^* \xleftarrow{61} A \xleftarrow{67} I$ |
| MDW 164 | 10% | +18.4 | +184 | 30 | $X \xleftarrow{19} C^* \xleftarrow{56} A \xleftarrow{63} I$ |

[1] Measured at $T_c$-$T_x$ except as noted.
[2] Transition temperature in degrees C. and phases as indicated in text.
[3] Measured at room temperature. tilt angle may not be saturated in this case.
[4] This mixture had a smectic A phase at room temperature and no measurements were made.

W82 (IV) is known to possess an enantiotropic ferroelectric C* phase with very low polarization density of the order of 1 nC/cm² and very low electro-optical switching speed of the order of 3 msec (1 μm thick layer, SSFLC geometry, 15 V/μm driving voltage). Mixtures of the compounds of the present invention possess ferroelectric C* phases with higher polarization density and/or faster switching speeds than W82.

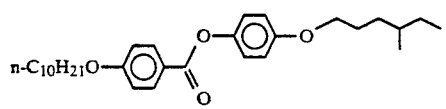

IV

An important aspect of the present invention is the finding that FLC compounds of formula II incorporating trans-1-methyl-(2,3-epoxy)alcohol diastereomers have properties as FLC dopants which are significantly different from those of formula III. Compounds of formula II can impact higher polarization densities in FLC mixtures than compounds of formula III. This property can be qualitatively compared in the different diastereomers by comparing the polarization densities of the pure diastereomers ($P_{ext}$), which are extrapolated from polarization densities of mixtures. The $P_{ext}$ of MDW 155 of formula II is +107, while that of the analogous diastereomer MDW 156 of formula III is −5.3, an approximate 20-fold difference. This difference can be discerned physically, since FLC mixtures containing the diastereomers of formula II will display higher polarization densities and faster switching speeds than FLC mixtures containing an equal amount of the corresponding diastereomer III.

It is believed that the difference in polarization densities of the compounds of formulas II and III is due to general and qualitatively independent of the structure of the Ar2 core, as indicated by the results shown in Table 1.

Variation in the structure of the cores and length and degree of branching in the R and R' groups of compounds encompassed in formulas I and II can affect the liquid crystal properties of the pure material or mixtures containing them. For example, some of the compounds of the present invention may possess smectic C* phases while others do not and the characteristics of any such smectic C* phases (i.e. stability, temperature range) may vary.

EXAMPLE 1

This example illustrates the procedures for synthesis of diastereomerically pure 1R-methyl-2S,3S-epoxy and 1S-methyl-2R,3R-epoxy alcohols 3 and 4.

A flame-dried, argon-filled three-necked flask fitted with a mechanical stirrer and containing 250 ml of $CH_2Cl_2$ was cooled to −10° C. (+)Diethyl-L-tartrate (+DET, 20 mmol), Ti(iso-$C_3H_7$)4 (15 mmol) and 4 g of dry, powdered molecular sieves were added to the flask and the resulting mixture was stirred for 20 min. Methyl allylic alcohol, 5-methyl-2-hex-3-enol, 1 where R'=isopropyl, (23.2 g, 100 mmol) was then added to the flask and the reaction mixture was stirred for another 20 min. at −10° C. The reaction mixture was then cooled to −40° C. and 50 mmol of t-butylhydroperoxide (TBHP) was added slowly over 5 min to the cold reaction mixture. During addition, the temperature of the reaction mixture rose to −30° C. The reaction mixture was stirred for 30 min. at this temperature, then warmed to −10° C. and stirred for an additional 6 hr. Water (20 ml)

was then added and the reaction mixture was stirred for 1 hr. to hydrolyze Ti(isoC$_3$H$_7$)$_4$. The reaction mixture was then filtered through a thick pad of celite. The yellow gelatinous precipitate obtained was washed generously with ether and the solvent was remove under vacuum. The resulting product residue was subjected to vacuum distillation with the epoxy alcohol, 1S,5-dimethyl-2S,3S-epoxypentanol, distilling at 45° C. and 10 mmHg to give 11.0 g of alcohol product, an 85% yield. The epoxy alcohol obtained at this stage contained a small amount of the 1R,2S,3S-diastereomer.

The methyl epoxy alcohol product mixture produced by enantioselective epoxidation (3+4, where R=isopropyl) (5.0 g, 38.5 mmol) was dissolved with 15.2 g (58 mmol) triphenylphosphine and 2.3 g (38.5 mmol) acetic acid in dry THF (60 ml). A solution of diisopropylazodicarboxylate (DIAD) (58 mmole) in 3 ml of dry THF was added dropwise to the reaction mixture over a period of 2 hr at room temperature. The course of the reaction was followed by thin layer chromatography (TLC) on silica plates. TLC of the reaction mixture showed two spots, at about Rf=0.54 and Rf=0.46, on silica plates run in 20% (v/v) ethylacetate/hexanes. The lower (Rf 0.46) spot was the major product (4, epoxy acetate) in which the S chiral center at C1 was inverted to the R configuration (Mitsunobu reaction). The reaction was stirred at room temperature for another 3 hr and solvent was removed under vacuum. The resulting residue was then subjected to flash chromatography on a silica column eluting with 4% (v/v) ethylacetate/hexanes. Pure inverted acetate 1R,5-dimethyl-2S,3S-epoxypentylacetate, having Rf of about 0.46, as noted above, was collected from the column. Eluting solvent was removed to afford 2.8 g of a clear liquid product (43% yield).

1R,5-dimethyl-2S,3S-epoxypentylacetate (2.5 g, 14.54 mmol) was dissolved in dry methanol, 5.2 g (30 mmol) of anhydrous K$_2$CO$_3$ was added to the solution and the reaction mixture was stirred at room temperature for 1 hr. Methanol was removed under vacuum and the resulting residue was partitioned between dilute brine and ether. The aqueous and organic layers were separated. The aqueous layer was extracted twice with 50 ml of ether. The ether layers were combined, washed sequentially with saturated NaHCO$_3$ (2×) and brine, dried with MgSO$_4$ and filtered. Solvent was removed under vacuum to give 1.72 g of diastereomerically pure 1R,5-dimethyl-2S,3S-epoxypentanol in 92% yield. The alcohol was further purified by flash chromatography on a silica column eluting with 8% (v/v) ethylacetate/hexanes.

Impure 1S-methyl-2S,3S-epoxy alcohol 3, where R'=isopropyl (2.6 g, 20 mmol), which contained a small amount of its 1R,2S,3S-diastereomer, was combined with 3.06 g (30 mmol) acetic anhydride in 5 ml of pyridine. The reaction mixture was cooled to −20° C. and stored overnight (approx. 18 hr.). The reaction mixture was then extracted with ether (3×100 ml). The organic layers were collected, washed with diluted brine (3×) and dried. Ether was removed under vacuum to give 3.0 g of acetate product, which was subjected to flash chromatography on silica eluting with 4% (v/v) ethylacetate/hexanes to give the diastereomerically pure 1S,5-dimethyl-2S,3S-epoxypentyl acetate (2.4 g). The acetate ran at about Rf=0.54 on silica TLC plates in 20%(v/v) ethylacetate/hexanes.

1S,5-dimethyl-2S,3S-epoxypentyl acetate (2.4 g, 14 mmol) was stirred with anhydrous K$_2$CO$_3$ (5.2 g, 30 mmol) in dry methanol for 2 hr. The workup and purification procedures used were those employed for the deprotection of the diastereomeric acetate, described above.

EXAMPLE 2

This example provides a representative procedure for the SN2 coupling of the chiral nonracemic methyl epoxy alcohols to p-benzyloxyphenol with inversion to give the 4'-(1-methyl-2,3-epoxy)alkoxy-p-benzyloxyphenols 5 and 7.

In an argon-flushed flask, 400 mg (2 mmol) of p-benzyloxyphenol, (BzOPhOH) 786 mg (3 mmol) of triphenylphosphine (PPh$_3$) and 260 mg of 1S,5-dimethyl-2S,3R-epoxypentanol were dissolved in 25 ml of dry THF. To this mixture, a solution of 666 mg (3.3 mmol) DIAD in 3 ml of dry THF was added dropwise over a period of 2 hr. The reaction mixture was stirred overnight at room temperature, after which the solvent was removed under vacuum. The residue was subjected to flash chromatography on a silica column eluting with 5% (v/v) ethylacetate/hexanes to give 524 mg of 4'-(1R-methyl-2S,3S-epoxy)alkoxy-4-benzyloxyphenyl ether.

The benzyloxyphenyl ether (524 mg, 1.68 mmol) was dissolved in 20 ml of ethanol in a 50 ml round-bottomed flask with a gas inlet. Hydrogen was bubbled through the reaction mixture and palladium hydroxide (10% on carbon, 90 mg) was then added with vigorous stirring. The reaction was followed by TLC and found to be complete in about 1 hr. The reaction mixture was then filtered through a pad of celite. The filtrate was collected and ethanol was remove under vacuum to give 372 mg of crude phenol product 5, where R' is isopropyl. The product was purified by flash chromatography on silica eluting with 15% (v/v) ethylacetate/hexanes.

In an analogous procedure, 242 mg (1.86 mmol) of the 1R,2S,3S alcohol 4, where R'=isopropyl, 370 mg (0.86 mmol) of p-benzyloxyphenol and 733 mg (2.78 mmol) of PPh$_3$ were dissolved in 25 ml of dry THF. To this mixture 586 mg (3.3 mmol) of DIAD in 3 ml dry THF was added dropwise over 2 hr. The reaction mixture was stirred overnight at room temperature after which solvent was removed under vacuum. The residue was subjected to flash chromatography on a silica column eluting with 5% (v/v) ethylacetate/hexanes to give 485 mg of benzyloxyphenylether product which was hydrogenated as described above. After removal of the ethanol solvent, the crude product was subjected to flash chromatography on a silica column eluting with 10% (v/v) ethylacetate/hexanes to give phenol 6, where R'=isopropyl.

EXAMPLE 3

This example illustrates representative procedures for the coupling of the substituted benzoylchloride with the 1-methyl-2,3-epoxyalkoxyphenols (5 and 6) to give the chiral nonracemic FLC phenylbenzoates (7 and 8).

Compound 5, where R'=isopropyl (222 mg, 1 mmol) and p-decyloxy-benzoylchloride (300 mg, 1 mmol) were dissolved in dry dichloromethane in an argon-flushed flask and the reaction mixture was cooled to 0° C. Triethylamine (3 equivalents) and a catalytic amount of dimethylaminopyridine (DMAP) were then added to the reaction mixture. The reaction mixture was stirred for 2 hr after which the solvent was removed under vacuum. The resulting residue was passed through a short silica column eluting with hexanes to give crude phenylbenzoate product 7, where R'=isopropyl and R=n-decyloxy. The product was further purified by crystallization from hexanes.

Compound 6, where R'=isopropyl (153 mg, 0.69 mmol) and p-decyloxybenzoylchloride (300 mg, 1 mol) were dissolved in dry chloromethane in an argon-flushed flask and the reaction mixture was cooled to 0° C. Triethylamine and DMAP were added, as above, and the reaction was stirred for 2 hrs. Solvent was removed under vacuum and the resulting residue was passed through a short silica column eluting with hexanes to give the crude phenylbenzoate 8, where R'=isopropyl and R=n-decyloxy. The product was further purified by crystallization from hexanes.

The invention has been described and illustrated by reference to several preferred embodiments, but it is not intended to limit the invention by doing so. For example, while as noted above, a single enantiomer of each chirally asymmetric compound has been prepared, it is intended that the invention encompass both enantiomers of each compound. It is also intended that the invention include mixtures of the two enantiomers of the same formula in which there is an excess of one enantiomer. It is further intended that the invention encompass not only the FLC dopant compounds, but also compositions or formulations in which these compounds are admixed with each other or with other compounds including LC and FLC materials.

We claim:

1. A chiral nonracemic compound of the formula:

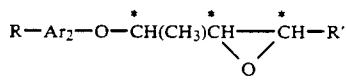

having a chiral tail group having three asymmetric carbons indicated by * wherein Ar$_2$ is a phenylpyrimidine or phenylpyridine, r is an alkyl or alkoxy group containing three to fifteen carbon atoms and R' is an alkyl group containing three to twelve carbon atoms.

2. The compound according to claim 1 in which R is an alkyl group having from three to fifteen carbon atoms.

3. The compound according to claim 2 wherein R is an alkyl group having from eight to twelve carbon atoms.

4. The compound according to claim 3 wherein R is a straight-chain alkyl group.

5. The compound according to claim 4 wherein R is an alkyl group containing eight or nine carbon atoms.

6. The compound according to claim 2 in which R' is an alkyl group having three to seven carbon atoms.

7. The compound according to claim 6 in which R' is an isopropyl group.

8. The compound according to claim 1 in which the chiral tail group is a 1R-methyl-2S,3S-epoxy or 1S-methyl-2R,3R-epoxy alcohol enantiomer.

9. The compound according to claim 8 in which the chiral tail group is a trans-1-methyl-2,3-epoxyalkoxy group.

10. The compound according to claim 9 wherein R is an alkyl group having from three to fifteen carbon atoms.

11. The compound according to claim 10 wherein R is an alkyl group having from eight to twelve carbon atoms.

12. The compound according to claim 11 wherein R is a straight-chain alkyl group.

13. The compound according to claim 12 in which R is an alkyl group containing eight or nine carbon atoms.

14. The compound according to claim 9 in which R' is an alkyl group having three to seven carbon atoms.

15. The compound according to claim 14 in which R' is an isopropyl group.

16. The compound according to claim 1 wherein Ar$_2$ is a phenylpyrimidine.

17. The compound according to claim 1 wherein Ar$_2$ is a phenylpryidine.

18. A chiral nonracemic compound having the formula:

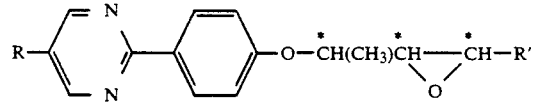

or

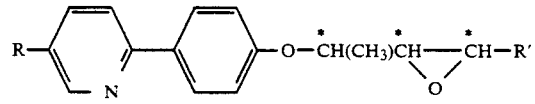

having a chiral tail group having three asymmetric carbons indicated by * wherein R is an alkyl or alkoxy group containing three to fifteen carbon atoms and R' is an alkyl group containing three to twelve carbon atoms.

19. The compound according to claim 18 in which the chiral tail group is a 1R-methyl-2S,3S-epoxy or 1S-methyl-2R,3R-epoxy alcohol enantiomer.

20. The compound according to claim 18 in which the chiral tail group is a trans-1-methyl-2,3-epoxyalkoxy group.

21. The compound according to claim 18 wherein R is an alkyl group having from three to fifteen carbon atoms.

22. The compound according to claim 21 wherein R is an alkyl group having from eight to twelve carbon atoms.

23. The compound according to claim 22 wherein R is a straight-chain alkyl group.

24. The compound according to claim 23 in which R is an alkyl group containing eight or nine carbon atoms.

25. The compound according to claim 18 in which R' is an alkyl group having three to seven carbon atoms.

26. The compound according to claim 25 in which R' is an isopropyl group.

* * * * *

UNITED STATES PATENT AND TRADEMARK OFFICE
CERTIFICATE OF CORRECTION

PATENT NO.   : 5,178,793

DATED        : Jan. 12, 1993

INVENTOR(S)  : Rohini T. Vohra; David M. Walba; Michael D. Wand

It is certified that error appears in the above-identified patent and that said Letters Patent is hereby corrected as shown below:

At column 3, line 65, please delete "1988". At column 11, line 8, please rewrite "45°." as --45°--. At column 12, lines 14-15, please rewrite "1S,5-dimethyl-2S,3R-epoxypentanol" as --1S,4-dimethyl-2S,3S-epoxypentan-1-ol--. At column 12, line 35, please rewrite "purified" as --removed--. At column 13, line 40, please rewrite "r" as --R--.

Signed and Sealed this

Twenty-first Day of December, 1993

Attest:

BRUCE LEHMAN

*Attesting Officer*     Commissioner of Patents and Trademarks